(12) United States Patent
Thomson et al.

(10) Patent No.: US 8,843,420 B2
(45) Date of Patent: Sep. 23, 2014

(54) DETERMINING WHETHER A MEASUREMENT SIGNATURE IS SPECIFIC TO A BIOLOGICAL PROCESS

(75) Inventors: Ty Matthew Thomson, Arlington, MA (US); Dexter Roydon Pratt, Reading, MA (US)

(73) Assignee: Selventa, Inc., Cambridge, MA (US)

( * ) Notice: Subject to any disclaimer, the term of this patent is extended or adjusted under 35 U.S.C. 154(b) by 95 days.

(21) Appl. No.: 13/213,404

(22) Filed: Aug. 19, 2011

(65) Prior Publication Data

US 2013/0046726 A1    Feb. 21, 2013

(51) Int. Cl.
*G06F 15/18*    (2006.01)
*G06F 19/12*    (2011.01)
*G06F 19/24*    (2011.01)

(52) U.S. Cl.
CPC .............. *G06F 19/12* (2013.01); *G06F 19/24* (2013.01)
USPC ......................................................... 706/12

(58) Field of Classification Search
CPC ........................ G06F 17/30032; G06N 99/005
USPC ...................................................... 706/12, 62
See application file for complete search history.

(56) References Cited

U.S. PATENT DOCUMENTS 7,519,519 B1 *    4/2009    Eynon et al. ...................... 703/2
2012/0129153 A1 *    5/2012    Martynov et al. .................. 435/5

OTHER PUBLICATIONS

Russell, S. and Norvig, P. Artificial Intelligence: A Modern Approach, second ed., 2003, pp. 114-119.*

* cited by examiner

*Primary Examiner* — Kakali Chaki
*Assistant Examiner* — Vincent Gonzales
(74) *Attorney, Agent, or Firm* — David H. Judson

(57) ABSTRACT

A "Specificity" statistic (or metric) is computed as a means to identify amplitude scores associated with a signature that can be attributed with high probability to a specific biological entity or process represented by the signature. Preferably, Specificity is computed by assessing a likelihood of a given null hypothesis, namely, that an amplitude score is not representative of the specific signature but, instead, is representative of a general trend in the applicable data set that can be measured by any signature that is comparable to the signature of interest. In a typical implementation, a first step to compute the Specificity metric is to construct a set of comparable signatures. Next, an amplitude score is computed for each of these signatures, preferably using the same data set. Then, the Specificity metric is computed, preferably as a two-tailed p-value, by placing the amplitude score for the signature of interest on a distribution of scores for the comparable signatures. Scores that have Specificity p-values less than a particular value, e.g., 0.05, are considered to be scores that can be attributed with high confidence to the signature of interest.

12 Claims, 2 Drawing Sheets

DETERMINING WHETHER A MEASUREMENT SIGNATURE IS SPECIFIC TO A BIOLOGICAL PROCESS

RELATED APPLICATION

This application is related to Ser. No. 13/149,022, filed May 31, 2010, titled "Method for quantifying amplitude of a response of a biological network."

TECHNICAL FIELD

This disclosure relates generally to methods and techniques for characterizing the response of biological networks.

BACKGROUND OF THE RELATED ART

Acquisition of large-scale data sets representing a variety of data modalities has become a crucial aspect of the characterization of experimental systems. Such a strategy affords a broad capture of biological information in a short time and with a relative small investment of effort. Rich datasets are collected in hopes that valuable biological insights might be gained. The amount of collected information, however, can be overwhelming, making interpretation of the data difficult, and subsequent detailed biological understanding elusive.

Researchers have developed several strategies to address the management of large-scale data sets, and these strategies offer some ability to interpret the data and develop biological insight. Many of these solutions are based on measurement enrichment. For example, Gene Set Enrichment Analysis determines whether members of a gene set tend to occur toward a top (or bottom) of a list, in which case the gene set is correlated with a phenotypic class distinction. Enrichment can also be incorporated with pathway analysis where, for example, specific measurements are associated with elements of a particular biological pathway. In addition to visually connecting measurements in this way, enrichment scores can be generated using a pathway to define the set of genes. Rather than identifying the upstream pathways that lead to the data, many of these enrichment-based solutions interpret the data from a "consequence" point of view, assessing the functional impact of the changes themselves. This approach, however, requires certain assumptions about the data and its impact, such as assuming mRNA expression is directly correlated to the activity of the encoded protein. Indeed, the correlation of mRNA to encoded protein abundance is variable. Focusing on strictly consequential perspectives also fails to capture a major facet of the data that can be harnessed from an upstream "causal" perspective. Additionally, from a use perspective, the output of many of these existing data interpretation strategies is a measure of statistical enrichment, ultimately yielding a Boolean decision about pathway enrichment/activation rather than a measure of activation intensity.

Alternative strategies have been described that focus on uncovering a characteristic "signature" of measurements that results from one or more perturbations to a biological process, and subsequently scoring the presence of that signature in additional data sets as a measure of specific activity of that process. Most previous work of this type involves identifying and scoring signatures that are correlated with a disease phenotype. These phenotype-derived signatures provide significant classification power, but the lack of a mechanistic or causal relationship between a single specific perturbation and the signature means that the signature may represent multiple distinct unknown perturbations that lead to the same disease phenotype. A number of studies, however, have focused instead on measuring causal signatures based on very specific upstream perturbations either performed directly in the system of interest, or from closely-related published data. Based on the simple, yet powerful, premise that modulation of cellular pathways and the components therein are associated with distinct signatures in measured node entities, causally-derived signatures enable the "cause" of the signature to be identified with high specificity from the measured "effect." These studies have demonstrated the great potential of applying a causal pathway scoring strategy to clinical problems, for example, by providing prognosis predictions in gastric cancer patients and indications of specific drug efficacy.

Given the vast potential of the information contained within large-scale data sets and the increasing ease at obtaining this data, new ways of mining understanding from these data sets have begun to be developed. Thus, for example, application Ser. No. 13/149,022, filed May 31, 2011, and commonly-owned, describes a method by which known techniques for causal pathway analysis of large data sets are extended to provide for a measure of intensity, which facilitates the comparison of biological states based on degree or amplitude of perturbation rather than comparison of likelihood of perturbation based on enrichment. According to that application, one or more measurement signatures are derived (e.g., from a knowledge base of casual biological facts), where a signature is a collection of measured node entities and their expected directions of change with respect to a reference node. The knowledge base may be a directed network of experimentally-observed casual relationships among biological entities and processes, and a reference node represents a potential perturbation to a biological entity or process (i.e., an entity that is hypothetically perturbed). A "degree of activation" of a signature is then assessed by scoring one or more "differential" data sets against the signature to compute an amplitude score, sometimes referred to as the "network perturbation amplitude" (NPA) metric. A "differential" data set is a data set having first and second conditions, e.g., a "treated" versus a "control" condition. In one embodiment, the amplitude score quantifies fold changes of measurements in the signature. A fold change is a number describing how much a quantity changes going from an initial to a final value.

While the above-described techniques provide significant advantages, it is desired to consider whether the computed NPA score is "specific" to the biological process described by the signature of interest or, rather, is a general property of the entire data set. For example, a score that indicated a two-fold increase in a given process holds less meaning if all measurements in the entire data set also increased two-fold. Thus, there remains a need to provide a measure (and methodology) by which scores that can be attributed with high probability to the specific biological entity or process (represented by the signature) can be determined.

The techniques disclosed herein address this need.

BRIEF SUMMARY

According to this disclosure, a "Specificity" statistic (or metric) is computed as a means to identify amplitude scores associated with a signature that can be attributed with high probability to a specific biological entity or process represented by the signature. Preferably, Specificity is computed by assessing a likelihood of a given null hypothesis, namely, that an amplitude score is not representative of the specific signature but, instead, is representative of a general trend in the applicable data set that can be measured by any signature that is comparable to the signature of interest. In a typical implementation, a first step to compute the Specificity metric is to construct a set of comparable signatures. Next, an amplitude score is computed for each of these signatures, preferably using the same data set. Then, the Specificity metric is computed, preferably as a two-tailed p-value, by placing the amplitude score for the signature of interest on a distribution of scores for the comparable signatures. Scores that have Specificity p-values less than a particular value, e.g., 0.05, are considered to be scores that can be attributed with high confidence to the signature of interest.

According to another aspect, a method of determining whether a signature is specific to a biological process begins by receiving the signature. Preferably, the signature is a collection of measured node entities and their expected directions of change with respect to a reference node. A degree of activation of the signature is then determined by scoring one or more data sets against the signature to compute an amplitude score. The determination of whether the signature is specific to the biological process associated with the signature computes a quantile from which a p-value, the Specificity metric, is generated. In particular, the quantile illustrates where the amplitude score falls within a distribution of scores of comparable signatures and, thus, the degree to which the amplitude score differs from the background data.

In one embodiment, a comparable signature is composed of measured node entities selected at random from a set of all measured node entities to produce a signature of the same size as the signature of interest. In another embodiment, a comparable signature is composed of measured node entities that have a similar number of upstream controllers as the measured node entities of the signature of interest, where the number of upstream controllers functions as an estimate of the likelihood of modulation of each measurement node. In yet another embodiment a comparable signature may be constructed as in the two previous embodiments, but may have a different size than the signature of interest.

The foregoing has outlined some of the more pertinent features of the invention. These features should be construed to be merely illustrative. Many other beneficial results can be attained by applying the disclosed invention in a different manner or by modifying the invention as will be described.

BRIEF DESCRIPTION OF THE DRAWINGS

For a more complete understanding of the present invention and the advantages thereof, reference is now made to the following descriptions taken in conjunction with the accompanying drawings, in which.

DETAILED DESCRIPTION

Figure 1:
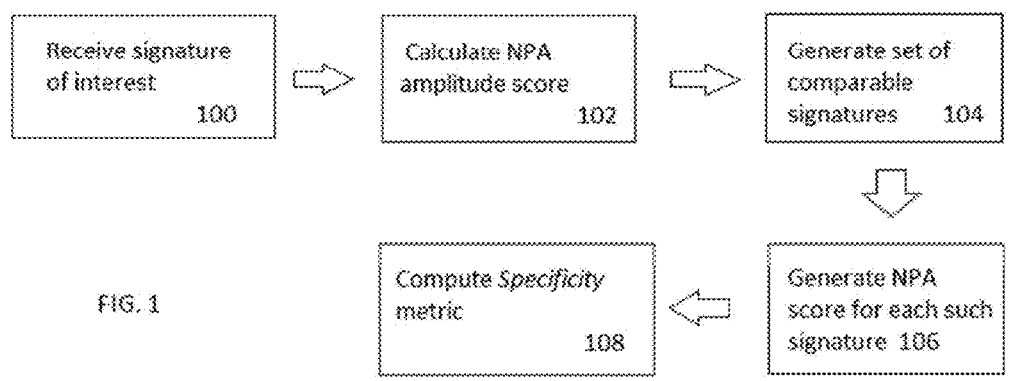
FIG. 1 is a process by which "Specificity" of an NPA score associated with a signature of interest is determined according to this disclosure.

The techniques herein, in one embodiment, take advantage of known systems and methods for assembling and mining life science data. In particular, it is known to manage and evaluate life science data using a large-scale, specialized, literature-derived knowledgebase of causal biological facts, sometimes referred to as a Knowledge Assembly Model (KAM). A system, method and apparatus of this type are described in commonly-owned U.S. Pat. No. 7,865,534, and U.S. Publication No. 2005/0165594, the disclosures of which are incorporated herein by reference. Familiarity with these known techniques is presumed. In addition to signatures derived from a casual knowledge base, there are other known techniques to derive the signature. Thus, in general, a signature is "received" from a source, which source may (but is not required to) be a casual knowledge base.

As described in Ser. No. 13/149,022, filed May 31, 2011, the disclosure of which is hereby incorporated by reference, it is known to extend these assembly and mining techniques to provide an "intensity" measure to provide for a high resolution comparison of biological states. As described in that application, there are several types of intensity measures that may be implemented, including, but not limited to, Strength, and Measured Abundance Signal Score (MASS).

As used herein, the following terms have the following definitions:

A "knowledge base" is a directed network, preferably of experimentally-observed casual relationships among biological entities and processes;

A "node" is a measurable entity or process;

A "measurement node" is a measured entity or process;

A "reference node" represents a potential perturbation to a node;

A "signature" is a collection of measurable node entities and their expected directions of change with respect to a reference node;

A "differential data set" is a data set that has data associated with a first condition, and data associated with a second condition distinct from the first condition; and A "fold change" is a number describing how much a quantity changes going from an initial to a final value, and is specifically computed by dividing the final value by the initial value.

A "quantile" is one of a series of points taken at regular intervals from a cumulative distribution function of a random variable.

As described in Ser. No. 13/149,022, one or more measurement signatures can be derived (e.g., from a knowledge base of casual biological facts), where a signature is a collection of measured node entities and their expected directions of change with respect to a reference node. Where a knowledge base is used to derive the signatures, preferably the knowledge base is a directed network of experimentally-observed casual relationships among biological entities and processes, and a reference node represents a potential perturbation. According to application Ser. No. 13/149,022, a "degree of activation" (referred to as "Strength" or "Measured Abundance Signal Score" in particular embodiments) of a signature is then assessed by scoring one or more "differential" data sets against the signature. The result of this computation is an amplitude score, measure or metric. A "differential" data set is a data set having first and second conditions, e.g., a "treated" versus "control" condition, a disease versus normal condition, a disease condition versus a different disease condition, a disease treated with a first drug versus the same disease treated with a second drug, a "responder" versus a "non-responder," a patient population versus a different patient population, pre- and post-drug treatment, pre- and post-development of a disease, pre- and post-remission of a disease, and so forth. The above examples are not intended to be limiting.

In one embodiment as described in Ser. No. 13/149,022, a signature is defined as a set of measurement node entities (for example, mRNAs) and their expected direction of change (whether they are increased or decreased) in response to a perturbation. An expected direction of change typically is a fixed value, such as +1, representing an increase, and −1, representing a decrease, although this is not a limitation. One or more scoring algorithms are then used to assess the "degree of activation" of each measurement signature. In general, the quantification approach herein (i.e., the "degree of activation" measures) validates the use of a broad, literature-derived knowledge base to score various aspects of biology that can be defined as very specific mechanisms (such as an individual protein activity) that are directly proximal to the data, or as a larger network of interest that is composed of a collection of individual mechanisms.

As a shorthand reference, but not by way of limitation, the "degree of activation" computed as described in Ser. No. 13/149,022 is sometimes referred to as a "network perturbation amplitude" or "NPA." As noted above, the disclosure in Ser. No. 13/149,022 describes several "types" of the degree of activation measure associated with a signature. The first of these types is a "strength" measure, which is a weighted average of adjusted log-fold changes of measured node entities in the signature, where the adjustment applied to the log-fold changes is based on their expected direction of change. As used herein, log refers to log 2 or log 10. Thus, the "strength" metric quantifies fold-changes of measurements in the signature.

The following is a representative example of a "strength-based" amplitude score of this type:

$$\text{Strength}(f) = \frac{\sum_i (1 - pval_i)^f \times direction_i \times \log_2(FC_i)}{\sum_i (1 - pval_i)^f}$$

In this example, $direction_i$, represents the expected direction of change according to the signature (e.g., +1, representing an increase, and −1, representing a decrease) of the $i^{th}$ measured node entity in the signature, $FC_i$, represents the measured fold-change of the $i^{th}$ measured node entity, $pval_i$ represents a p-value for $FC_i$, f is a constant that controls the degree to which the influence each fold change is weighted according to its p-value, N is a number of measured node entities in the signature, and the sum over all i is the sum over all measured node entities in the signature. This "strength at f" (or p-value adjusted Strength) measure thus is the weighted geometric mean of the ratios of the measurement where the weighting factors are derived from the p-values, and the ratios are adjusted for their predicted direction of change.

An alternative "unweighted" Strength measure with weight=1 (equivalently, f=0) is derived according to the following function:

$$\text{Strength} = \frac{\sum_i direction_i \times \log_2(FC_i)}{N}$$

In particular, "unweighted" Strength is the geometric mean of the ratios of the measurements of quantities predicted by to change according to a signature, adjusted for the direction of the prediction.

Strength assumes that the ratio of change of each measurement (e.g., a measured gene) is the basis of the calculation for the metric. Thus, two measurements have the same impact on the metric if they change by the same ratio, regardless of the absolute value of their measured values. In certain circumstances, however, the impact of a change in a measured gene may be more likely to depend on the ratio of change, because the transcripts of critical genes in control systems such as transcription factors may be present in small numbers but have large effect. However, NPA metrics are meant to assess the magnitude of perturbation of the reference node of a signature, rather than the impact of changes elicited by the signature. In attempting to measure the amplitude of a process, the quantity of the effects actually observed may be more important than what those changes might cause. Thus, as an alternative to the Strength measures described above, the degree of activation measure may be based on Measured Abundance Signal Score (MASS). As also described in Ser. No. 13/149,022, a MASS is an NPA based on absolute changes of nodes that represent some measurable physical quantities. In one variant, this approach is applicable to any measurement technique that quantifies a physical measurable in a manner such that measurements are proportional to absolute quantities across all measurement nodes (i.e., the measurements for different nodes can be compared directly). Thus, as one example of this latter approach, the metric is a count that represents a change in absolute node quantities in a direction supporting an increase in a process described by the signature, divided by an average of a total absolute quantity of the nodes. This approach to computing the degree of activation measure thus quantifies the absolute change in the nodes (corrected for the expected direction of change of each node in the signature) compared to the total quantity of the nodes.

Specificity

As has been described, the purpose of an NPA metric is to measure the amplitude of a network response to a stimulus, and to facilitate a comparison of network activity levels between different perturbations or conditions. To derive additional value from an NPA score, it is desired to consider whether the computed NPA score is "specific" to the biological process described by the signature of interest or, rather, is a general property of the entire data set (i.e., the score for the signature of interest occurs by chance). This disclosure describes a method to compute a so-called "Specificity" metric that provides a way to make this determination. In general, "Specificity" is an assessment of an NPA score's specificity across specific experimental conditions. It answers the question of whether the NPA score results specifically from the biology that underlies a particular signature (i.e., it is different from general trends in the data set).

This disclosure describes a technique for determining Specificity and, in particular, whether an NPA score results from general trends in a data set (i.e., occurs by chance) or, rather, results from specific biology underlying the signature.

Preferably, the Specificity metric is determined by evaluating the likelihood of a given null hypothesis as a means to identify scores that can be attributed with a given probability to the specific biology underlying signatures. The null hypothesis is that the NPA metric score is not truly representative of any specific biology as measured by a specific signature, but rather is representative of a general effect that can be measured by any comparable signature. As used herein, and as will be described in more detail below, one embodiment of a "comparable" signature is a signature composed of measurement nodes that have similar likelihood of modulation as the measurement nodes in the signature of interest.

Specificity provides a way to diagnose the source of a particular NPA score. A score that meets the Specificity criteria presumably is an accurate score for that signature. On the other hand, a score that does not meet the Specificity criteria may still reflect the amplitude of activation of the process represented by the signature, but the score cannot be attributed with high confidence to the process represented by the signature. Additionally, if a score is very weak (i.e., close to zero), the biology driving the score becomes less relevant, in which case it would be expected that the score would have weak Specificity as well.

Figure 2:
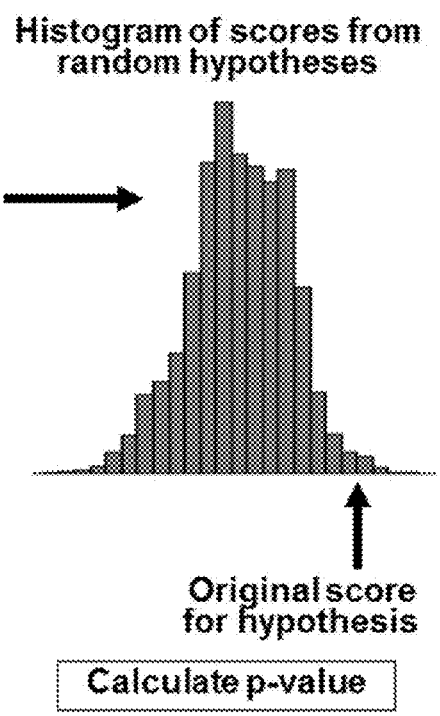
FIG. 2 illustrates a distribution of NPA scores for comparable signatures (to the signature of interest in FIG. 1) and showing Specificity as a two-tailed p-value, according to this disclosure.

A general technique for determining Specificity is now described. As shown in FIG. 1, a first step 100 to computing Specificity is to receive a signature of interest. At step 102, an NPA score is calculated, such as in the manner described in Ser. No. 13/149,022, although this is not a limitation. At step 104, a set of comparable signatures is constructed. Next, at step 106, an NPA score is computed for each of these signatures using the same dataset. Finally, at step 108, Specificity is computed, preferably as a two-tailed p-value, by placing the amplitude score for the signature of interest on the distribution of scores for the comparable signatures. This is illustrated in FIG. 2. Given the null hypothesis, preferably scores that have Specificity p-values less than 0.05 are considered to be scores that can be attributed with high confidence to the signature of interest.

In computing the Specificity statistic, relevant comparable signatures should be used. In one embodiment, a simple comparable signature is composed of measured node entities selected at random from a set of all measured node entities to produce a signature of the same size as the signature of interest. An advantage of this embodiment is that is does not require a knowledgebase to construct the comparable signatures. Typically, such a sample will be biased towards showing a weaker (or no) change. This makes the amplitude score for the signature of interest appear more unlikely to have occurred by chance given the null hypothesis—and thus be more specific—than might have otherwise been expected. In an alternate embodiment, a comparable signature is composed of measured node entities that have a similar number of upstream controllers as the measured node entities of the signature of interest, where the number of upstream controllers functions as an estimate of the likelihood of modulation of each measurement node. Comparable signatures constructed in this manner provide a more stringent test to assess the Specificity of amplitude scores than the comparable signatures described in the previous embodiment. In yet another embodiment a comparable signature may be constructed as in the two previous embodiments, but may have a different size than the signature of interest.

In an illustrative embodiment, a body of causal knowledge (such as a knowledgebase available commercially from Seleventa, Inc., of Cambridge, Mass.) is consulted to construct a comparable signature for transcriptomic data in the following manner. A number of upstream controllers (i.e., distinct entities upstream of a gene in causal statements in the knowledge base) for each gene in the entire dataset, including the genes in the signature, are identified. Typically, the number of upstream controllers reflects the number of different experiments or perturbations that caused the gene to be modulated, and it acts as a naïve estimate for the likelihood of each gene being modulated in the current experiment. For example, a gene that is only regulated under very specific circumstances is unlikely to be modulated in many data sets that are curated in the knowledgebase. Thus, only a few entities that causally regulate the gene will exist in the knowledgebase. In contrast, a gene whose expression is modulated by a large number of experimental perturbations is likely to be modulated in many data sets that are represented in the knowledgebase, and thus the knowledgebase is likely to contain knowledge of many entities that causally regulate the gene. Therefore, in one approach, a comparable signature is constructed by replacing each gene in the original signature with another measured gene with a similar number of upstream controllers.

To accomplish this, preferably all measured genes are ranked (based on their number of upstream controllers in the knowledgebase) and then divided into cadres of a fixed number of measurement nodes. To avoid having a cadre containing only a few measurement nodes (for example, when the number of nodes is not divisible by the desired cadre size), the cadre that contains measurement nodes with the fewest number of upstream controllers is allowed to have more measurement nodes than the other cadres. For example, if a cadre size of 100 measurement nodes is used, the cadre that contains measurement nodes with the fewest number of upstream controllers has between 100 and 199 members. This example scenario is merely representative. Comparable signatures are then constructed by swapping each measurement node in the original signature for another measurement node from within the same cadre. In this manner, a comparable signature is the same size as the original signature and contains the same distribution of frequently and in-frequently modulated measurement nodes. This process enables the construction of alternative signatures that are as comparable as possible to the signature of interest, given the knowledge available in the knowledgebase.

As described with respect to FIG. 1, NPA scores are computed (for each comparable signature), and these scores are then sorted, preferably into ascending order. In one embodiment, the Specificity is then generated as follows. In particular, the fraction of scores that are greater than and less than the score for the original signature are counted, and the lesser of these two values is doubled to arrive at a two-tailed p-value. This p-value is called the Specificity, as previously noted.

Figure 3:
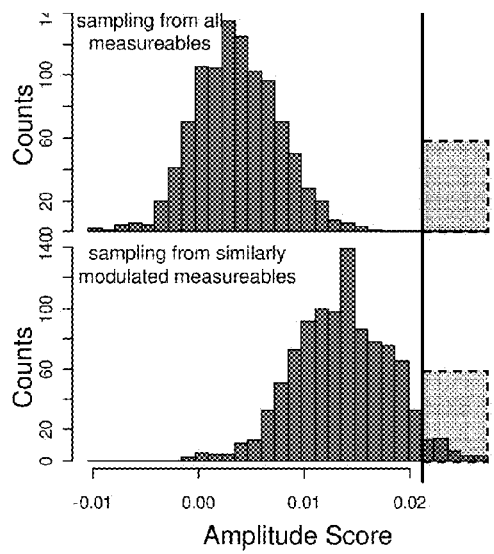
FIG. 3 illustrates histograms of MASS scores for signatures comparable to a signature representing NF-κB activation, where the measurement node entities in the comparable signatures are (top) selected at random from all measurements or (bottom) selected from measurement node entities with similar likelihood of modulation as the measurement node entities in the signature representing NF-κB activation.

FIG. 3 illustrates a histogram of MASS scores for signatures comparable to a signature of interest representing NF-κB activation. In this example, the top histogram results from selecting measurement nodes at random from all measurement nodes (resulting in a Specificity p-value of 0), and the bottom histogram results from selecting measurement nodes with comparable likelihood of modulation (resulting in a Specificity p-value of 0.072). The solid line indicates the NF-κB signature MASS score. In this example, the Specificity p-value was computed by doubling the total fraction of counts that were greater than this score (the fraction of counts in the boxes).

Generalizing, preferably the Specificity p-value is computed from the position of the NPA score on a distribution of NPA scores computed from comparable signatures. Comparable signatures are determined, in one embodiment, by swapping each measurement in the signature of interest for another measurement selected at random from a data set, resulting in signatures of the same size as the original signature. In the alternative, comparable signatures are determined by swapping each measurement in the signature for another measurement from the data set that is equally likely (or substantially equally likely) to be modulated (i.e., equally likely to be affected by the given experiment) as the measurement it replaces. In this alternative, the likelihood that a measurement will be modulated can be estimated by a number of biological entities and perturbations that are known (e.g., from a knowledgebase) to modulate that measurement.

Figure 4:
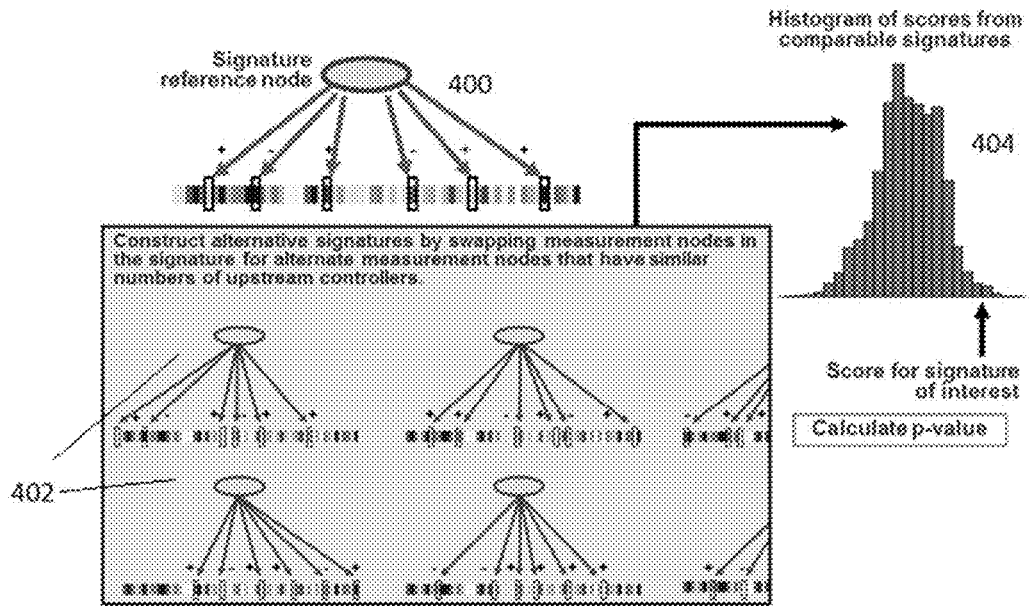
FIG. 4 illustrates a technique for computing the Specificity p-value by swapping measurements from a signature of interest for alternative measurement nodes that have similar numbers of controllers.

FIG. 4 illustrates the technique for computing the Specificity p-value and, in particular, by swapping measurement nodes from the signature of interest 400 for alternate measurement nodes (that have similar numbers of controllers) to generate the comparable signatures 402. These alternative signatures are used to generate the histogram of scores 404 against which the original score is placed. This drawing illustrates how the described technique computes a quantile (where the original score falls into the distribution of scores of comparable signatures evaluated on the same data) and turns it into a p-value.

The techniques described herein are implemented using computer-implemented enabling technologies such as described in commonly-owned, co-pending applications U.S. Publication No. 2005/00038608, No. 2005/0165594, No. 2005/0154535, and No. 2007/0225956. These patent applications, the disclosures of which are incorporated herein by reference, describe a casual-based systems biology modeling tool and methodology. In general, this approach provides a software-implemented method for hypothesizing a biological relationship in a biological system that uses a database comprising a multiplicity of nodes representative of biological elements, and relationship descriptors describing relationships between nodes, the nodes and relationship descriptors in the database comprising a collection of biological assertions from which one or more candidate biological assertions are chosen. After selecting a target node in the database for investigation, a perturbation is specified for the target node. In response, given nodes and relationship descriptors of the database that potentially affect or are affected by the target node are traversed. In response to data generated during the traversing step, candidate biological assertions can be identified for further analysis. These biological assertions, and the nodes described therein, comprise the signature of interest for the target node (i.e., the signature's reference node).

Aspects of this disclosure (such as the calculation of the Specificity metrics) may be practiced, typically in software, on one or more machines or computing devices. Generalizing, a machine or computing device (a "computing entity") typically comprises commodity hardware and software, storage (e.g., disks, disk arrays, and the like) and memory (RAM, ROM, and the like). The particular computing entities used in the system are not a limitation of the present invention. A given machine includes network interfaces and software to connect the machine to a network in the usual manner. The subject matter or features thereof may be implemented as a standalone product, or as a managed service using a set of machines, which are connected or connectable to one or more networks. More generally, the product or service is provided using a set of one or more computing-related entities (systems, machines, processes, programs, libraries, functions, or the like) that together facilitate or provide the inventive functionality described above. In a typical implementation, the service comprises a set of one or more computers. A representative machine is a network-based server running commodity (e.g. Pentium-class) hardware, an operating system (e.g., Linux, Windows, OS-X, or the like), an application runtime environment (e.g., Java, .ASP), and a set of applications or processes (e.g., AJAX technologies, Java applets or servlets, linkable libraries, native code, or the like, depending on platform), that provide the functionality of a given system or subsystem. A display may be used to provide an output of the Specificity metric. As described, the product or service (or any function thereof) may be implemented in a standalone server, or across a distributed set of machines, or in any a tablet or handheld computing device. Typically, a server or computing device connects to the publicly-routable Internet, an intranet, a private network, or any combination thereof, depending on the desired implementation environment.

Having described our invention, what we now claim is as follows.

The invention claimed is:

1. A method, comprising:
   receiving a signature that is a collection of measurement node entities and their expected directions of change with respect to a reference node, the signature having an associated degree of activation that has been determined by scoring one or more data sets against the signature to compute an amplitude score; and
   determining, in a computing entity, whether the signature's amplitude score is specific to a biological process or occurs by chance in the one or more data sets, wherein the determining step evaluates a Specificity metric associated with the amplitude score and includes computing the Specificity metric as a p-value that is computed from a position of the amplitude score on a distribution of amplitude scores computed from comparable signatures, wherein a comparable signature has a same size as the signature;
   wherein the comparable signature is generated by replacing at least one measurement in the signature for another measurement from the data set that is equally likely to be modulated as the measurement it replaces.

2. The method as described in claim 1 wherein the comparable signature is generated by replacing at least one measurement in the signature for another measurement from a data set selected at random.

3. The method as described in claim 1 wherein the comparable signature is generated by replacing each measurement in the signature for another measurement from the data set that is equally likely to be modulated as the measurement it replaces.

4. A method of determining Specificity of an amplitude score of interest associated with a signature, comprising:
   generating a set of signatures that are comparable to the signature;
   scoring, using a computing entity, each of the comparable signatures to generate an amplitude score associated with each such comparable signature; and
   computing a p-value from a position of the amplitude score of interest on a distribution of amplitude scores computed from the comparable signatures;
   wherein a comparable signature is generated by replacing at least one measurement in the signature for another measurement from the data set that is equally likely to be modulated as the measurement it replaces.

5. The method as described in claim 4 further including using the p-value to determine whether the amplitude score of interest is specific to a biological process represented by the signature or occurs by chance.

6. The method as described in claim 4 wherein a comparable signature is generated by replacing at least one measurement in the signature for another measurement from a data set selected at random.

7. The method as described in claim 4 wherein a comparable signature is generated by replacing each measurement in the signature for another measurement from the data set that is equally likely to be modulated as the measurement it replaces.

8. Apparatus, comprising:
   a processor;

computer memory holding computer program instructions executed by the processor to determine a Specificity of an amplitude score of interest associated with a signature by the following operations:

generating a set of signatures that are comparable to the signature;

scoring each of the comparable signatures to generate an amplitude score associated with each such comparable signature; and computing a p-value from a position of the amplitude score of interest on a distribution of amplitude scores computed from the comparable signatures;

wherein a comparable signature is generated by replacing at least one measurement in the signature for another measurement from a data set that is equally likely to be modulated as the measurement it replaces.

9. The apparatus as described in claim 8 further including a display upon which the distribution of amplitude scores computed from the comparable signatures is rendered.

10. The apparatus as described in claim 8 wherein a comparable signature has a same size as the signature.

11. The apparatus as described in claim 8 wherein a comparable signature is generated by replacing at least one measurement in the signature for another measurement from a data set selected at random.

12. The apparatus as described in claim 8 wherein a comparable signature is generated by replacing each measurement in the signature for another measurement from the data set that is equally likely to be modulated as the measurement it replaces.

* * * * *